US010639285B2

(12) United States Patent
Gopi et al.

(10) Patent No.: US 10,639,285 B2
(45) Date of Patent: May 5, 2020

(54) PROCESS FOR PREPARATION OF BIOAVAILABLE WHITE CURCUMIN—A UNIQUE BLEND OF HYDROGENATED CURCUMINOIDS

(71) Applicant: Aurea Biolabs Private Limited, Cochin, Kerala (IN)

(72) Inventors: Sreeraj Gopi, Cochin (IN); Joby Jacob, Cochin (IN); Robin George, Cochin (IN)

(73) Assignee: Aurea Biolabs Private Limited, Cochin Kerala (IN)

( * ) Notice: Subject to any disclaimer, the term of this patent is extended or adjusted under 35 U.S.C. 154(b) by 0 days.

(21) Appl. No.: 15/107,100

(22) PCT Filed: Dec. 4, 2015

(86) PCT No.: PCT/IB2015/059348
§ 371 (c)(1),
(2) Date: Jun. 21, 2016

(87) PCT Pub. No.: WO2016/097914
PCT Pub. Date: Jun. 23, 2016

(65) Prior Publication Data
US 2017/0258743 A1    Sep. 14, 2017

(30) Foreign Application Priority Data

Dec. 15, 2014  (IN) ............ 6309/CHE/2014

(51) Int. Cl.
*A61K 31/121*  (2006.01)
*A23L 33/105*  (2016.01)
(Continued)

(52) U.S. Cl.
CPC .......... *A61K 31/121* (2013.01); *A23L 33/105* (2016.08); *A61K 47/6951* (2017.08);
(Continued)

(58) Field of Classification Search
None
See application file for complete search history.

(56) References Cited

U.S. PATENT DOCUMENTS 5,266,344 A * 11/1993 Mimura ............... A23L 3/3481
426/546
6,653,327 B2 * 11/2003 Majeed ................ A61K 8/35
424/400

(Continued)

FOREIGN PATENT DOCUMENTS

| CA | 2735631 A | * | 1/2012 |
| IN | 200500786 | | 6/2009 |
| WO | 2007103435 | | 9/2007 |

OTHER PUBLICATIONS

ChemFaces—Tetrahydrocurcumin, http://www.chemfaces.com/natural/Tetrahydrocurcumin-CFN90583.html; accessed Oct. 12, 2018. (Year: 2018).*

(Continued)

*Primary Examiner* — Dominic Lazaro
(74) *Attorney, Agent, or Firm* — J. Peter Paredes; Rosenbaum IP, P.C.

(57) ABSTRACT

The present invention discloses a process for preparation of white curcumin from purified curcuminoids. The curcuminoids are obtained by solvent extraction and crystallization of dried turmeric powder. The autoclave is charged with ethyl acetate and the 95% purity curcuminoids mixture is added to and stirred for uniformity at room temperature. 5% (w/w) of 10% palladium carbon is added to the reaction mixture and allowed for hydrogenation in the presence of hydrogen gas at 2 lbps pressure and stirred continuously for 15 hours. Once the reaction is completed, the reaction mixture is filtered and washed with ethyl acetate. The ethyl acetate is distilled off and crude mass is stirred with water to obtain a solid precipitate. Finally, the solid obtained is (Continued)

filtered and dried to pale brown crystals of white curcumin. White curcumin is encapsulated with beta-cyclodextrin, which exhibited increased bioavailability. White curcumin also exhibited anti-oxidant and chemopreventive activities.

9 Claims, 4 Drawing Sheets

(51) Int. Cl.
*C07C 45/62* (2006.01)
*C07C 41/20* (2006.01)
*C08B 37/16* (2006.01)
*A61K 47/69* (2017.01)
*C07C 41/26* (2006.01)
*C07C 37/00* (2006.01)

(52) U.S. Cl.
CPC .............. *C07C 37/00* (2013.01); *C07C 41/20* (2013.01); *C07C 41/26* (2013.01); *C07C 45/62* (2013.01); *C08B 37/0015* (2013.01); *A23V 2002/00* (2013.01)

(56) References Cited

U.S. PATENT DOCUMENTS

| | | | |
|---|---|---|---|
| 2008/0031980 A1* | 2/2008 | Rodriguez | A61K 36/9066 424/773 |
| 2010/0179103 A1* | 7/2010 | Desai | A61K 47/48969 514/58 |
| 2011/0135627 A1* | 6/2011 | LaMotta | A61K 9/0014 424/94.65 |
| 2018/0071187 A1* | 3/2018 | Goenka | A61K 8/42 |

OTHER PUBLICATIONS

ChemFaces—Hexahydrocurcumin, http://www.chemfaces.com/natural/Hexahydrocurcumin-CFN97749.html; accessed Oct. 12, 2018. (Year: 2018).*

ChemFaces—Octahydrocurcumin, http://www.chemfaces.com/natural/Octahydrocurcumin-CFN90584.html; accessed Oct. 12, 2018. (Year: 2018).*

Muhammed, M., & Prakash, L., A lighter Skin Tone and More . . . With Natural Actives, Sabinsa Corporation presentation (2008), accessed at https://www.drmajeed.com/pdf/articles/2008ALighterSkinToneandMore.pdf on Sep. 24, 2019 (Year: 2008).*

* cited by examiner

|  | After Blend % | After Cooking % |
|---|---|---|
| Bread (180 degree) | 0.074 | 0.072 |
| Cake (200 degree) | 0.073 | 0.070 |
| Cookies 160 degree 12 min | 0.070 | 0.070 |
| Cookies 180 degree 15 min | 0.069 | 0.068 |

FIGURE 5

PROCESS FOR PREPARATION OF BIOAVAILABLE WHITE CURCUMIN—A UNIQUE BLEND OF HYDROGENATED CURCUMINOIDS

TECHNICAL FIELD OF THE INVENTION

The present invention relates to a process for preparation of bioavailable white curcumin from curcuminoids. More particularly, the invention discloses a process, which includes catalytic hydrogenation of pure curcuminoids obtained from *Curcuma longa*, commonly known as turmeric. The process results in the formation of pure crystals of white curcumin. The present invention also discloses white curcumin with its biological properties useful in treatment of various diseases.

BACKGROUND OF THE INVENTION

Curcumin, chemically known as 1,7 bis (4-hydroxy-3-methoxy phenyl)-1,6 heptadiene-3,5-dione belongs to a curcuminoid class of the popular Indian spice *Curcuma longa*, a perennial herbaceous plant of Zingiberaceae (ginger) family, which is cultivated in India, China and other tropical countries. The rhizome is known for its pharmacological properties and has been used in food and Ayurvedic medicines since thousands of years for its medicinal properties. Curcumin is known for its use in inflammatory conditions, pain, liver disorders, and wide variety of pulmonary, gastrointestinal and skin diseases.

Curcuminoids are linear diarylheptanoids derived from turmeric and are natural phenols that impart yellow color to turmeric. Natural curcuminoids are poorly soluble in water. Hence, the curcuminoids are synthesized using chemical methods to increase the solubility and bioavailability.

Curcuminoids are traditionally used in the treatment of arthritis, gastrointestinal disorders, skin wounds, inflammation, cancers, cystic fibrosis, heart burn, Alzheimer's disease etc. Curcuminoid is an effective antioxidant with the ability to scavenge free radicals generated in the body as a result of various metabolic processes. Curcuminoids are also useful as food supplement.

Tetrahydrocurcuminoid is a colorless hydrogenated phenolic compound derived from curcuminoids and is known for its anti-oxidant activities, skin protection and inhibition of tyrosinase. The lack of yellow color and biological activities render the use of tetrahydrocurcuminoid in food and cosmetic applications. However, the poor systemic bioavailability due to poor solubility in water limits the use of the compound.

Solubility of tetrahydrocurcuminoid was determined in various vehicles such as oils, co-surfactants, surfactants etc. and also by using different polymers. Different methods are also employed to increase the solubility and hence, the bioavailability of tetrahydrocurcuminoid. Several conventional techniques based on physical parameters such as heat, pH, and complexations with metal ions, serum has been proposed to increase the solubility. Even though, curcumin exhibits more pharmacological properties, the amount of total curcuminoids absorbed is less.

The chemical and synthetic methods are also proposed to synthesize the white curcumin. However, these methods involve complicated steps with moderate purity of the final product. In addition, most of the proposed processes use the re-crystallization step, which increases the complexity of the process.

The PCT application numbered PCT/US2001/032441 titled "Process of making and method of use of tetrahydrocurcuminoids to regulate physiological and pathological events in the skin and mucosa cells" discloses a method for producing tetrahydrocurcuminoids by saturating two olefinic bonds in a mixture of curcuminoids. This process is carried out by mixing ethyl acetate and curcuminoids at room temperature. Further, catalytic hydrogen transfer reagent is added followed by palladium carbon with continuous stirring. The mixture is cooled and the resultant mixture is filtered and washed with toluene to obtain toluene extract. The toluene extract is further washed with hydrochloric acid and water. Finally, toluene is removed under vaccum to obtain a paste of tetrahydrocurcuminoids. The method involves continuous steps of washing and filtration, which may increase the cost of the process and also may reduce the purity of the final product.

The PCT application numbered PCT/US2000/008711 titled "Use of tetrahydrocurcuminoids to regulate physiological and pathological events in the skin and mucosa" discloses a method for producing tetrahydrocurcuminoids by saturating two olefinic bonds in a mixture of curcuminoids. The method involves the steps of mixing ethyl acetate and curcuminoids at room temperature. The hydrogen transfer reagent is added, followed by palladium carbon as catalyst with continuous stirring. The mixture is filtered after cooling and washed with toluene to obtain toluene extract. The toluene extract is further washed with hydrochloric acid and water. Toluene is removed under vaccum to obtain a paste or slurry. The slurry is vaccum dried to obtain tetrahydrocurcuminoids. However, the method involves multiple steps of filtration, which increases the cost of the process and also reduces the purity of the final product. In addition, toluene is toxic in nature.

The PCT application numbered PCT/IN2005/000337 titled "Process for producing enriched fractions of tetrahydroxycurcumin and tetrahydrotetrahydroxy-curcumin from the extracts of *Curcuma longa*" describes a process for producing an enriched fraction of tetrahydoxycurcumin containing tetrahydroxycurcumin, demethylcurcumin, demethylmonodemethoxycurcumin, bisdemethoxycurcumin and colorless tetrahydroderivatives. The process consists of demethylation of natural curcumins. The enriched fraction of tetrahydroxycurcumin is subjected to hydrogenation to get colorless tetrahydrotetrahydroxycurcumin enriched fraction. The enriched fractions of tetrahydroxycurcumin and colorless tetrahydrotetrahydroxycurcumin exhibit potent antioxidative action and reduce inflammation. However, the process may not result in purified form of tetrahydoxycurcumin.

Curcumin processed using the conventional methods is associated with low bioavailability and less heat stability. Hence, there is a need for an improved process for synthesis of white curcumin, which exhibits higher solubility and bioavailability.

SUMMARY OF THE INVENTION

In order to simplify the purification steps and to obtain high purity white curcumin, the present invention describes a process for preparation of bioavailable white curcumin from curcuminoids. The purified curcuminoids are obtained from *Curcuma longa*. The invention discloses a simple and specific method to synthesize white curcumin by reducing the curcuminoids in the presence of metallic catalyst.

White curcumin is a mixture of tetrahydrocurcuminoids, hexahydrocurcuminoids and octahydrocurcuminoids at the concentration of 75-80%, 15-20% and 3-5% respectively. Pure curcuminoids are obtained from the *Curcuma longa*. A dried turmeric powder is subjected to solvent extraction to isolate the curcuminoids, which are further subjected to crystallization to obtain the purified curcuminoids.

The two olefinic bonds or two keto groups in curcuminoids are saturated using hydrogen transfer reaction in the presence of the metallic catalyst. An autoclave is charged with ethyl acetate. The solution is further charged with the purified curcuminoids and stirred to uniformity at room temperature. After stirring, the metallic catalyst palladium carbon is added to the solution. The mixture is subjected to hydrogenation and subsequently stirred.

The completion of the reaction is confirmed using Thin Layer Chromatography (TLC) by analyzing the presence of curcuminoid analogs. The TLC used in the present invention is silica pre-coated plate of 0.25 mm thickness with hexane and ethyl acetate in the ratio of 7:3.

Once the reaction is completed, the reaction mixture is filtered through cotton canvas filter cloth to remove the palladium carbon and washed with ethyl acetate. Ethyl acetate is further distilled off to obtain a crude mass. The crude mass is stirred with water until a solid precipitate is formed. Finally, the solid precipitate is filtered and dried to obtain pale brown crystals of white curcumin.

White curcumin is encapsulated with beta-cyclodextrin to improve the bioavailability. The white curcumin thus obtained exhibits high solubility and bioavailability compared to curcumin. White curcumin is a strong anti-oxidant and chemo preventive in nature. White curcumin exhibits heat stability and hence is useful as food supplement and is colorless and useful in cosmetics.

BRIEF DESCRIPTION OF DRAWINGS

FIG. 5 illustrates the heat stability of white curcumin in different food samples.

DETAILED DESCRIPTION OF THE INVENTION

In order to make the matter of the invention clear and concise, the following definitions are provided for specific terms used in the following description.

The term "Curcumin" means the principal curcuminoid found in turmeric, which is a member of the ginger family.

The term "Bioavailability" is a measure of presence of drug in the systemic circulation once taken orally in terms of solubility, dispersibilty etc.

The term "Solubility" means the property of any compound to dissolve in a solid, liquid, or gas to form a homogeneous solution.

The term "Antioxidant" means a substance that removes potentially damaging oxidizing agents in a living organism.

The present invention discloses the process for preparation of bioavailable white curcumin. White curcumin is prepared from curcuminoids isolated from *Curcuma longa*.

The process of preparing white curcumin from curcuminoids involves the processing and purification of curcuminoids.

The dried turmeric powder is subjected to solvent extraction to isolate the curcuminoid fraction. The isolated curcuminoid fraction is subjected to crystallization to remove the impurities and to obtain the purified curcuminoids.

Figure 1:
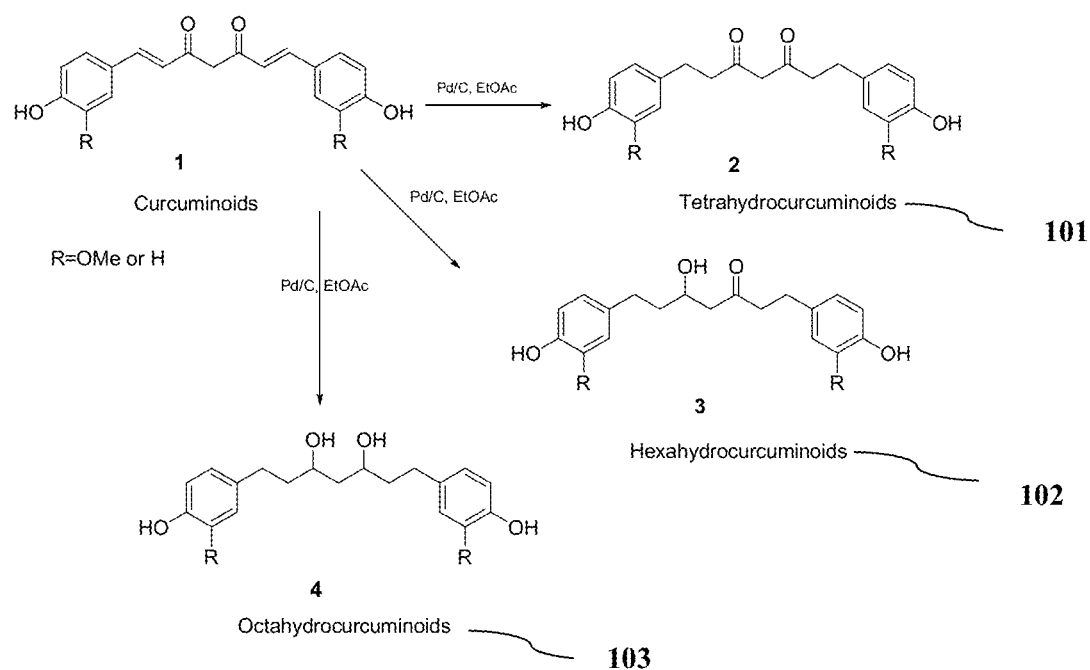
FIG. 1 illustrates a structure of white curcumin, which is a mixture of tetrahydrocurcuminoids, hexahydrocurcuminoids and octahydrocurcuminoids.

FIG. 1 illustrates a structure of white curcumin, which is a mixture of tetrahydrocurcuminoids, hexahydrocurcuminoids and octahydrocurcuminoids. White curcumin is a mixture of tetrahydrocurcuminoids 101, hexahydrocurcuminoids 102 and octahydrocurcuminoids 103 at the concentrations of 75-80%, 15-20% and 3-5% respectively.

Figure 2:
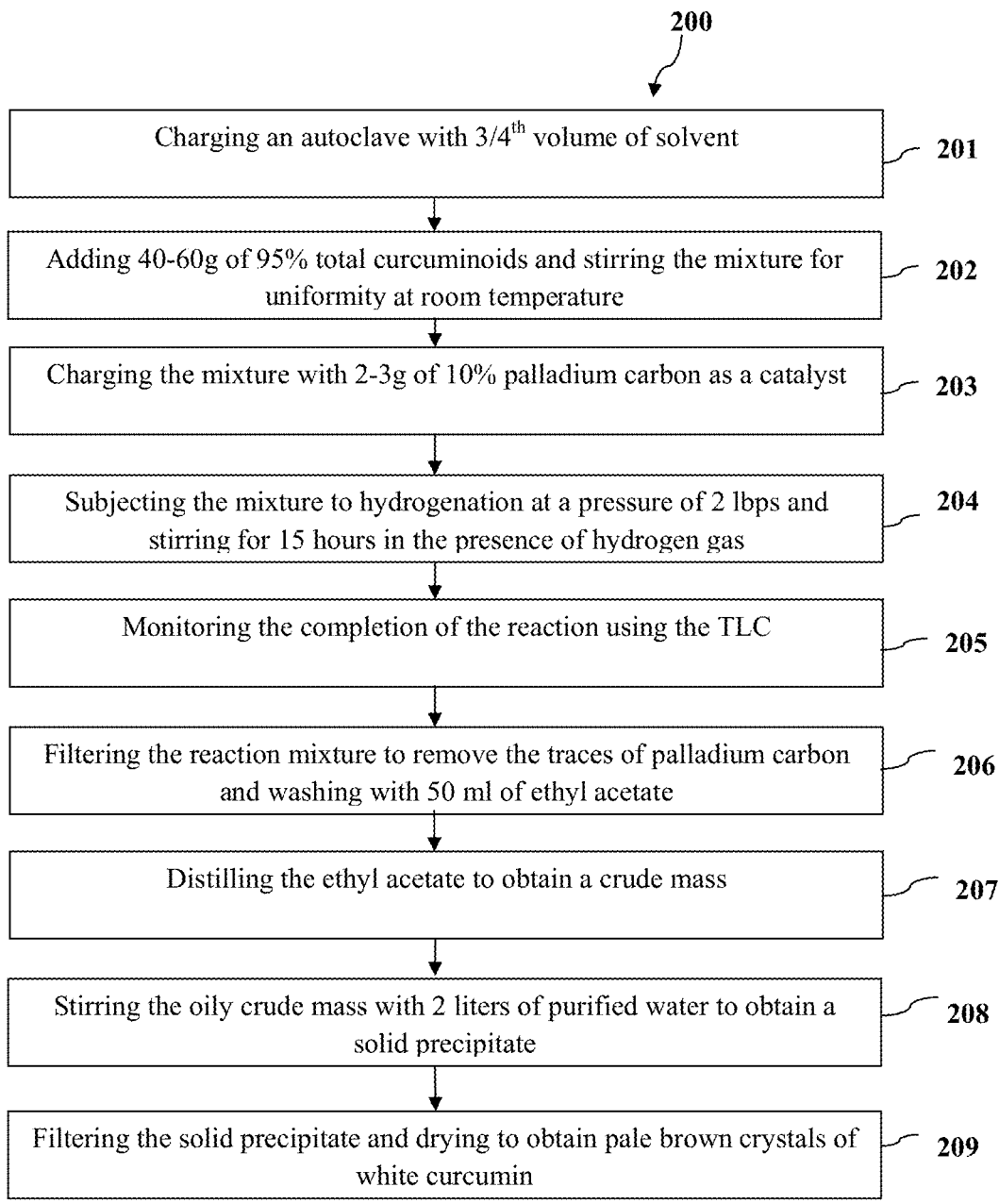
FIG. 2 illustrates a flow chart for process of preparation of white curcumin from the purified curcuminoids.

FIG. 2 illustrates a flow chart for process of preparation of white curcumin from the purified curcuminoids. The process 200 starts at the step 201 of charging an autoclave with $\frac{3}{4}^{th}$ volume of ethyl acetate, which is used as a solvent. At step 202, 40-60 g of 95% total curcuminoids is added to the organic solvent to form a reaction mixture and the mixture is stirred for uniformity at room temperature. At step 203, mixture is charged with 2-3 g of 10% palladium carbon, which acts as a catalyst and promotes the faster reaction. At step 204, the mixture is subjected to hydrogenation at a pressure of 2 lbps and subsequently stirred for 15 hours in the presence of hydrogen gas. This allows the reaction to occur in the presence of catalyst and reduction reaction of the curcuminoids is allowed. At step 205, the completion of the reaction is monitored using the Thin Layer Chromatography (TLC). TLC is performed using the pre-coated silica plates of 0.25 mm thickness with the solvent medium of hexane and ethyl acetate in the ratio of 7:3. At step 206, the reaction mixture is filtered through cotton canvas filter cloth to remove the traces of palladium carbon and washed with 50 ml of ethyl acetate. At step 207, the ethyl acetate is distilled off to obtain a crude mass. At step 208, the oily crude mass is stirred with 2 liters of purified water until a solid precipitate is formed. Finally at step 209, the solid precipitate is filtered and dried to obtain pale brown crystals with a yield of 36 g-54 g. The pale crystals are white curcumin containing tetrahydrocurcuminoids, hexahydrocurcuminoids and octahydrocurcuminoids at the concentration of 75-80%, 15-20% and 3-5% respectively. The use of the solvent in the said process is not only restricted to ethyl acetate but also methanol and ethanol are used as organic solvents during reduction of curcuminoids.

In order to improve the bioavailability of white curcumin, white curcumin is encapsulated with beta-cyclodextrin. Cyclodextrins belongs to family of cyclic oligonucleotides with a hydrophilic outer surface and a lipophilic central activity. Cyclodextrins are relatively large molecules with higher number of hydrogen donors and acceptors and hence do not permeate lipophilic membranes. Beta-cyclodextrin is used as complexing agent to increase the aqueous solubility of white curcumin. The increased solubility is associated with increased bioavailability.

Figure 3:
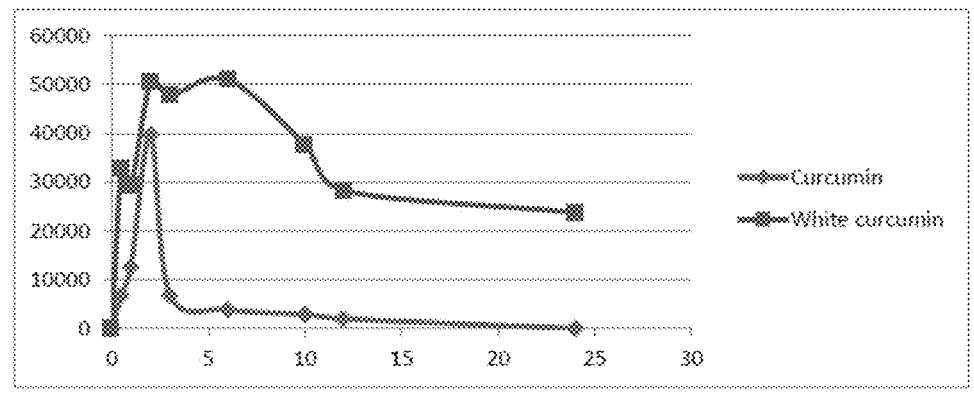
FIG. 3 illustrates the absorption of curcumin and white curcumin in the blood plasma.

FIG. 3 illustrates the absorption of curcumin and white curcumin in the blood plasma. The results showed that the absorption of white curcumin is at $6^{th}$ hour whereas in case of curcumin, the absorption is at 2 hours. White curcumin exhibited higher rate of absorption compared to curcumin with increased residence time even at $24^{th}$ hour whereas the concentration of absorbed curcumin diminished rapidly in the blood plasma.

Figure 4:
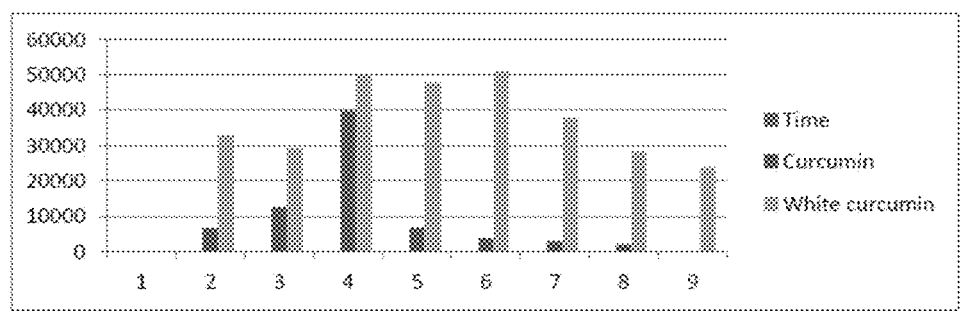
FIG. 4 illustrates the bio-equivalence of curcumin and encapsulated white curcumin in the blood plasma of rat.

FIG. 4 illustrates the bio-equivalence of curcumin and encapsulated white curcumin in the blood plasma of rat. The study of bio-equivalence is carried in female Sprague Dawley rats with a body weight of 150 g-170 g. The rats are administered with 25 mg/kg body weight of encapsulated white curcumin or 600 mg/kg body weight of curcumin. The blood samples are collected and analyzed at High Performance Liquid Chromatography (HPLC) at different time intervals. The bio-equivalent studies showed that the recommended dosage of encapsulated white curcumin is 250 mg per day in human and is equivalent to 1-2 g of encapsulated white curcumin per day. The encapsulated white curcumin exhibited higher rate of absorption by improving the permeability and increasing the residence time in jejunum and thus increasing the bioavailability.

FIG. 5 illustrates the heat stability of white curcumin in different food samples. White curcumin is added as a food ingredient in foods such as bread, cake and cookies. White curcumin is added at the concentration of 0.074% to bread, 0.073% to cake, 0.069% and 0.070% to cookies baked at 160° C. for 12 minutes and 180° C. for 15 minutes respectively. The results showed that heat stability of white curcumin at normal cooking temperature i.e. 120° C.-200° C. is appreciable. After cooking, the concentration of white curcumin did not exhibit significant degradation. White curcumin exhibited concentration of 0.072% in bread, 0.070% in cake and 0.070% and 0.068% in cookies baked at 160° C. for 12 minutes and 180° C. for 15 minutes respectively. The recommended dose of white curcumin as food ingredient is 0.25%-0.3%. White curcumin did not exhibit degradation before and after cooking and did not exhibit altered organoleptic characters such as taste, flavor, color and texture.

Example 1

Synthesis of White Curcumin from Curcuminoids

An autoclave is charged with ¾$^{th}$ volume of the ethyl acetate, which is used as a solvent. 50 g of 95% of total curcuminoids are added to the ethyl acetate solution and is stirred continuously for uniformity to form a reaction mixture at room temperature. To the reaction mixture, 2-3 g of 10% palladium carbon is added, which acts as a catalyst to accelerate the chemical reaction. The reaction mixture is subjected to hydrogenation at a pressure of 2 lbps and subsequently stirred for 15 hours in the presence of hydrogen gas. This allows the reaction to occur in the presence of catalyst and allows the reduction reaction of the curcuminoids. At this point, the completion of the reaction is monitored using TLC, which is performed using the pre-coated silica plates of 0.25 mm thickness with the solvent medium of hexane and ethyl acetate in the ratio of 7:3. After monitoring the completion of the reaction, the reaction mixture is filtered through cotton canvas filter cloth to remove the traces of palladium carbon and washed with 50 ml of ethyl acetate. After filtration, the ethyl acetate is distilled off to obtain a crude mass. The crude mass is oily in nature and is stirred with 2 liters of purified water which forms a solid precipitate. Finally, the solid precipitate is filtered and dried to obtain pale brown crystals of white curcumin. Approximately 35 g of the white curcumin is obtained by the above process and the white curcumin is a mixture of tetrahydrocurcuminoids, hexahydrocurcuminoids and octahydrocurcuminoids at the concentration of 75-80%, 15-20% and 3-5% respectively.

White curcumin exhibits higher antioxidant activity and free radical scavenging activity than curcumin by improving the lipid peroxidation in liver and plasma. White curcumin also exhibits larvicidal activity against some parasites. White curcumin exhibits anticancer activity and synergistic activity in combination with 5-fluorouracil in patient with colon cancer.

White curcumin thus obtained is of high purity and exhibits increased bioavailability and solubility. Further, white curcumin is useful in different formulations for treatment of various diseases and also as food supplement and in cosmetics due to the pale or colorless nature.

We claim:

1. A composition of a white curcumin with enhanced bioavailability, wherein the white curcumin comprises a mixture of 75-80% tetrahydrocurcuminoids, 15-20% hexahydrocurcuminoids and 3-5% octahydrocurcuminoids, wherein the white curcumin is synthesized by palladium carbon catalyzed hydrogenation of purified curcuminoids obtained from *Curcuma longa*.

2. The composition as claimed in claim 1, wherein the white curcumin is encapsulated in beta-cyclodextrin.

3. The white curcumin as claimed in claim 1, wherein the rate of absorption and residence time of the white curcumin is high in comparison to curcumin.

4. The white curcumin as claimed in claim 1, wherein the white curcumin scavenges free radicals generated in the body.

5. The white curcumin as claimed in claim 1, wherein the white curcumin possesses heat stability at a normal cooking temperature of 120° C.-200° C.

6. A process for preparation of a composition of white curcumin with enhanced bioavailability of claim 1, the process comprising the steps of:
   (a) charging an autoclave with ¾th volume of an organic solvent;
   (b) adding 40-60 g of 95% total curcuminoids obtained from *Curcuma longa* to the organic solvent to form a reaction mixture and stirring the reaction mixture for uniformity at room temperature;
   (c) adding 2-3 g of 10% palladium carbon as catalyst to the reaction mixture;
   (d) subjecting the reaction mixture obtained in step (c) to hydrogenation at pressure of 2 lbps and stirring the reaction mixture for 15 hours in the presence of hydrogen gas;
   (e) monitoring completion of the hydrogenation in step (d) using Thin Layer Chromatography (TLC) in order to obtain a completed reaction mixture;
   (f) filtering the completed reaction mixture through a cotton canvas filter cloth in order to obtain a filtrate by removing traces of palladium carbon from the completed reaction mixture, and washing the filtrate with 50 ml of ethyl acetate;
   (g) distilling the filtrate washed with ethyl acetate in order to remove the ethyl acetate and obtain a crude mass of white curcumin;
   (h) stirring the crude mass of white curcumin with 2 liters of purified water in order to obtain a solid precipitate of white curcumin;
   (i) filtering and drying the solid precipitate of white curcumin in order to obtain a white curcumin with enhanced bioavailability, wherein the white curcumin comprises a mixture of 75-80% tetrahydrocurcuminoids, 15-20% hexahydrocurcuminoids and 3-5% octahydrocurcuminoids.

7. The process as claimed in claim 6, wherein the organic solvent used is selected from a group consisting of ethyl acetate, methanol and ethanol.

8. The process as claimed in claim 1, further comprising a step of encapsulating the white curcumin obtained in step (i) with beta-cyclodextrin.

9. The process as claimed in claim 1, wherein the yield of the white curcumin obtained in step (i) is 36 g-54 g.

* * * * *